(12) United States Patent
Leung et al.

(10) Patent No.: US 8,748,104 B1
(45) Date of Patent: Jun. 10, 2014

(54) TROPONIN I PROTEIN BINDING COMPOUNDS

(71) Applicant: eNano Health Limited, Shatin, New Territories (HK)

(72) Inventors: Patrick Shau-park Leung, Arcadia, CA (US); Yuk Yu Leon, Shatin (HK); Yun Chung Chow, Shatin (HK)

(73) Assignee: eNano Health Limited, Shatin, New Territories (HK)

( * ) Notice: Subject to any disclaimer, the term of this patent is extended or adjusted under 35 U.S.C. 154(b) by 0 days.

(21) Appl. No.: 13/901,302

(22) Filed: May 23, 2013

Related U.S. Application Data

(60) Provisional application No. 61/758,556, filed on Jan. 30, 2013.

(51) Int. Cl.
*C12Q 1/68* (2006.01)

(52) U.S. Cl.
USPC .......................................... 435/6.12; 435/198

(58) Field of Classification Search
None
See application file for complete search history.

*Primary Examiner* — Jennifer Pitrak McDonald
(74) *Attorney, Agent, or Firm* — Edwards Wildman Palmer LLP; Jeffrey D. Hsi

(57) ABSTRACT

The invention provides aptamers capable of binding to the skeletal Troponin I protein useful as diagnostics of skeletal muscle damage in which the skeletal Troponin I protein has been implicated.

16 Claims, 3 Drawing Sheets

A)

B)

A)

B)

TROPONIN I PROTEIN BINDING COMPOUNDS

CROSS-REFERENCE TO RELATED APPLICATIONS

The present application claims priority benefit under 35 U.S.C. §119(e) of U.S. Provisional Patent Application Ser. No. 61/758,556, filed Jan. 30, 2013. The disclosure of this application is incorporated herein by reference.

BACKGROUND OF THE INVENTION

Troponin together with tropomyosin, regulate the binding of myosin to actin. Troponin is a trimeric protein composed of Troponin subunits I, C and T. Troponin C binds calcium ions, Troponin T binds to tropomyosin and troponin I binds to actin. This calcium-dependent interaction serves to position the tropomyosin along the actin filament during muscle contraction. Troponins are used as diagnostic biomarkers for cardiac injury.

Detection of skeletal muscle injury is hampered by a lack of commercially available assays for serum markers specific for skeletal muscle. Although CK is the most common serum marker for skeletal muscle injury, it is not ideal for several reasons, including lack of tissue specificity, inability to reveal damage to specific skeletal fiber types (fast or slow), and inappropriately low values when glutathione concentrations are decreased because of liver or multiple-organ failure. Skeletal muscle troponin-I is the marker of choice for detection of muscle injury because unlike myoglobin and heart-type FABP it is expressed exclusively in skeletal muscle. Myoglobin and heart-type FABP are useful markers of skeletal muscle injury in the absence of cardiac damage. Skeletal troponin I (sTnI), with its two distinct isoforms [fast (fsTnI) and slow (ssTni)], like cTnI and cTnT, may have an advantage over conventional markers for detecting skeletal muscle injury. Moreover, because sTnI exists in 2 isoforms, slow (ssTni) and fast (fsTnI), corresponding to slow- and fast-twitch muscles, respectively, it could provide insight into differential injury/recovery of specific fiber types.

SUMMARY OF THE INVENTION

The invention is directed to an aptamer and method of use. More particularly, the invention is directed to an aptamer and a detection method relating to the skeletal Troponin I protein. The invention provides aptamers capable of binding to the skeletal Troponin I protein useful as diagnostics of skeletal muscle damage in which the skeletal Troponin I protein has been implicated. The invention also provides for complexes, therapeutic agents, kits, methods of making, and methods of using the aforementioned (e.g., diagnostic, therapeutic methods).

In one aspect, the invention is an aptamer comprising one of the following nucleotide sequences:

```
                                          (SEQ ID NO: 1)
    5'-GGG ATG GGG TGG GTG GCC AGC GAT T-3', (SEQ ID NO: 2)
    5'-TTA GGG GTG GTG TGG TTG GCA ATT C-3',
```

In another aspect, the invention is an aptamer herein that specifically binds to skeletal Troponin I protein.

In another aspect, the invention is an aptamer herein, wherein the dissociation constant ($K_d$) between the aptamer and the skeletal Troponin I protein ranges from 5 nanomole (nM) to 37.7 nM.

In another aspect, the invention is an aptamer herein having a 5' end modified by a thiol group, a biotin label (e.g., biotinyl), a luminescent label including Firefly luciferase and *Renilla luciferase*; a fluorescent label including fluorescein isothiocyanate (FITC), phycoerythrin (PE), Cy3, and Cy5; or enzymes including alkaline phosphatase (AP), horse radish peroxidase (HRP).

In another aspect, the invention is an aptamer herein comprising 10 to 80 nucleotides.

Another aspect is a detection method for detecting the skeletal Troponin I protein in a sample, the detection method comprising: providing an aptamer herein; mixing the sample and the aptamer, such that the skeletal Troponin I protein in the sample and the aptamer bind to form a skeletal Troponin I-aptamer complex; and detecting the skeletal Troponin I protein or the aptamer in the skeletal Troponin I-aptamer complex.

In another aspect, the invention is a detection method herein, further comprising communicating the level of troponin I detected (e.g., oral, written, electronic medium). In another aspect the communication is to a health care provider.

In another aspect, the invention is a detection method herein, wherein the aptamer is labeled with a thiol group, a biotin label, a luminescent label including Firefly luciferase and *Renilla luciferase*; a fluorescent label including fluorescein isothiocyanate (FITC), phycoerythrin (PE), Cy3, and Cy5; or enzymes including alkaline phosphatase (AP), horse radish peroxidase (HRP).

The invention is further directed to a detection method of norketamine, where the detection method, using the Luminex detection system, is highly sensitive, compared to conventional colorimetric detection method, for example ELISA.

In another aspect, the invention is a detection method herein adapted for detecting the skeletal Troponin I protein in a sample, the detection method comprising: providing a plurality of beads covalently bonded to the skeletal Troponin I protein; mixing the beads and a labeled aptamer herein, such that the skeletal Troponin I protein on the beads bind with the labeled aptamer; adding strepavidin-phycoerythrin conjugates to the sample mixed with the beads, such that the strepavidin-phycoerythrin conjugates bind with the labeled aptamer; removing the unbound strepavidin-phycoerythrin conjugates; and detecting the strepavidin-phycoerythrin conjugates bound to the beads through the labeled aptamer.

In another aspect, the invention is a detection method herein wherein the labeled aptamer is labeled with a biotin label (i.e., biotinylated).

Another aspect is an aptamer-bead complex comprising an aptamer herein.

In another aspect, the invention is an aptamer-bead complex further comprising a label moiety.

Another aspect is a method of making an aptamer-bead complex herein comprising mixing the beads with an aptamer herein.

In another aspect, the invention is a method of making an aptamer-bead complex herein further comprising mixing in a strepavidin-phycoerythrin conjugate.

Another aspect is a kit comprising an aptamer herein and instructions for use to detect troponin I.

In another aspect, the invention is a kit, wherein the aptamer is conjugated to a bead.

Another aspect is a composition comprising skeletal troponin I protein on a bead, an aptamer herein, and a strepavidin-phycoerythrin conjugate.

In another aspect, the invention is a composition wherein the aptamer is biotinylated.

Another aspect is a therapeutic compound comprising an aptamer herein covalently bonded to a molecule useful to modulate skeletal troponin I protein function.

Another aspect is a method of treating a subject having a disease or disorder comprising administering to the subject a compound or composition herein.

In another aspect, the invention is a method herein wherein the disease or disorder is modulated by skeletal troponin I protein.

Another aspect is a method of detecting disease or disorder in a subject comprising: mixing a subject sample and an aptamer herein, such that the skeletal Troponin I protein in the sample and the aptamer bind to form a skeletal Troponin I-aptamer complex; and detecting the skeletal Troponin I protein or the aptamer in the skeletal Troponin I-aptamer complex.

In another aspect, the invention is a method herein wherein the disease or disorder is a muscular disease or disorder (e.g., muscle injury, muscle toxicity, drug-induced muscle toxicity).

In another aspect, the invention is a method herein further comprising communicating the results of the method to a health care provider.

In light of the foregoing, the aptamer of the invention is capable of specifically binding to the skeletal Troponin I protein, and the detection method for the skeletal Troponin I protein adopting the aptamer thus has high sensitivity.

BRIEF DESCRIPTION OF THE DRAWINGS

The accompanying drawings are included to provide further understanding, and are incorporated in and constitute a part of this specification. The drawings illustrate exemplary embodiments and, together with the description, serve to explain the principles of the disclosure.

DETAILED DESCRIPTION OF THE INVENTION

Figure 1:
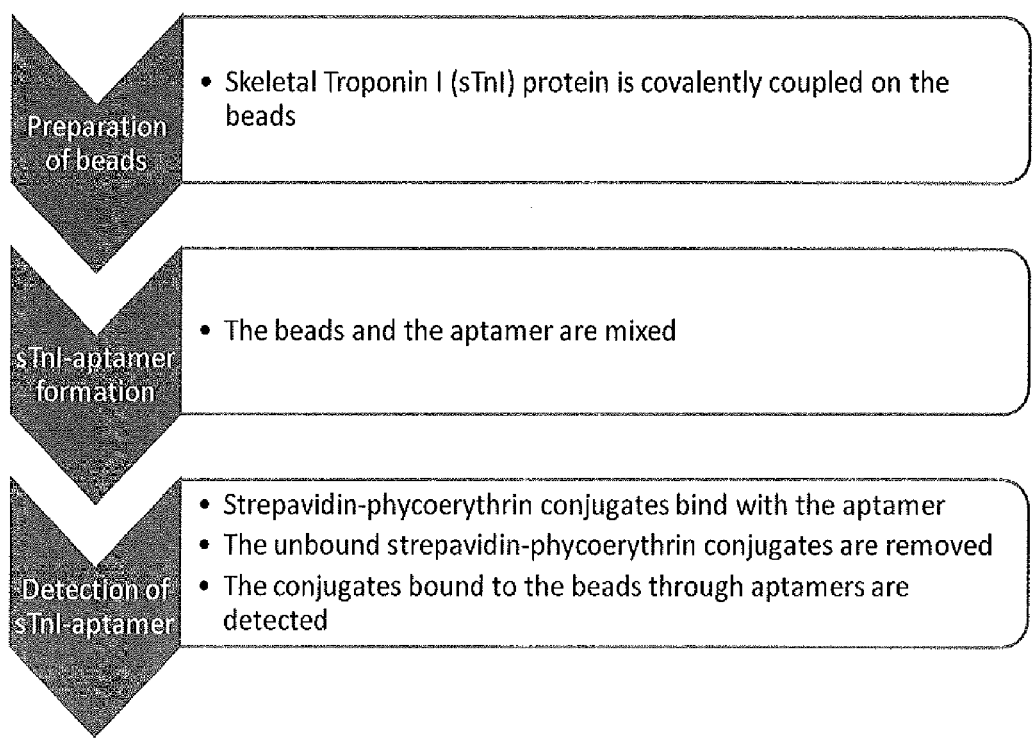
FIG. 1 shows a schematic flow chart of a detection method for a skeletal Troponin I protein according to an embodiment of the invention.

As used herein, the terms "aptamer", "compound", "protein", "nucleotide sequence", "nucleic acid" (including those specifically delineated herein), includes the pharmaceutically acceptable salts of said compound, its hydrates, and solvates.

The term "patient" or "subject" includes human and other mammalian subjects that receive either prophylactic or therapeutic treatment.

As used herein, "mammal" refers to any mammal including but not limited to human, mouse, rat, sheep, monkey, goat, rabbit, hamster, horse, cow or pig.

In addition, some of the compounds of this invention have one or more double bonds, or one or more asymmetric centers. Such compounds can occur as racemates, racemic mixtures, single enantiomers, individual diastereomers, diastereomeric mixtures, and cis or trans or E or Z double isomeric forms. All such isomeric forms of these compounds are expressly included in the present invention. A compound of the present invention will include not only a stereoisomeric mixture, but also individual respective stereoisomers substantially free from one another stereoisomers. The term "substantially free" as used herein means less than 25% of other stereoisomers, preferably less than 10% of other stereoisomers, more preferably less than 5% of other stereoisomers and most preferably less than 2% of other stereoisomers, are present. Methods of obtaining or synthesizing diastereomers are well known in the art and may be applied as practicable to final compounds or to starting material or intermediates. Other embodiments are those wherein the compound is an isolated compound.

Acids commonly employed to form pharmaceutically acceptable salts include inorganic acids such as hydrogen bisulfide, hydrochloric, hydrobromic, hydroiodic, sulfuric and phosphoric acid, as well as organic acids such as para-toluenesulfonic, salicylic, tartaric, bitartaric, ascorbic, maleic, besylic, ftimaric, gluconic, glucuronic, formic, glutamic, methanesulfonic, ethanesulfonic, benzenesulfonic, lactic, oxalic, para-bromophenylsulfonic, carbonic, succinic, citric, benzoic and acetic acid, and related inorganic and organic acids. Such pharmaceutically acceptable salts thus include sulfate, pyrosulfate, bisulfate, sulfite, bisulfite, phosphate, monohydrogenphosphate, dihydrogenphosphate, metaphosphate, pyrophosphate, chloride, bromide, iodide, acetate, propionate, decanoate, caprylate, acrylate, formate, isobutyrate, caprate, heptanoate, propiolate, oxalate, malonate, succinate, suberate, sebacate, fumarate, maleate, butyne 1,4 dioate, hexyne 1,6 dioate, benzoate, chlorobenzoate, methylbenzoate, dinitrobenzoate, hydroxybenzoate, methoxybenzoate, phthalate, terephathalate, sulfonate, xylenesulfonate, phenylacetate, phenylpropionate, phenylbutyrate, citrate, lactate, O-hydroxybutyrate, glycolate, maleate, tartrate, methanesulfonate, propanesulfonate, naphthalene-1-sulfonate, naphthalene-2-sulfonate, mandelate and the like salts.

Numerous methods are available for the chemical synthesis of candidate compounds. Such compounds can be synthesized from readily available starting materials using standard synthetic techniques and methodologies known to those of ordinary skill in the art. Synthetic chemistry transformations and protecting group methodologies (protection and deprotection) useful in synthesizing the compounds identified by the methods described herein are known in the art and include, for example, those such as described in R. Larock, Comprehensive Organic Transformations, VCH Publishers (1989); T. W. Greene and P. G. M. Wuts, Protective Groups in Organic Synthesis, 2nd ed., John Wiley and Sons (1991); L. Fieser and M. Fieser, Fieser and Fieser's Reagents for Organic Synthesis, John Wiley and Sons (1994); L. Paquette, ed., Encyclopedia of Reagents for Organic Synthesis, John Wiley and Sons (1995), and subsequent editions thereof.

Compounds of the invention can be administered as pharmaceutical compositions by any conventional route, in particular parenterally such as intravenously or by subcutaneous or intramuscular injections; enterally, e.g., orally, e.g., in the form of tablets or capsules, topically, e.g., in the form of lotions, gels, ointments or creams, or in a nasal or suppository form for localized delivery. Pharmaceutical compositions comprising a compound of the present invention in free form or in a pharmaceutically acceptable salt form in association with at least one pharmaceutically acceptable carrier or diluent can be manufactured in a conventional manner by mixing, granulating or coating methods. For example, oral compositions can be tablets or gelatin capsules comprising the active ingredient together with a) diluents, e.g., lactose, dextrose, sucrose, mannitol, sorbitol, cellulose and/or glycine; b) lubricants, e.g., silica, talcum, stearic acid, its magnesium or calcium salt and/or polyethyleneglycol; for tablets also c) binders, e.g., magnesium aluminum silicate, starch paste, gelatin, tragacanth, methylcellulose, sodium carboxymethylcellulose and or polyvinylpyrrolidone; if desired d) disintegrants, e.g., starches, agar, alginic acid or its sodium salt, or effervescent mixtures; and/or e) absorbents, colorants, flavors and sweeteners. Injectable compositions can be aqueous isotonic solutions or suspensions, and suppositories can be prepared from fatty emulsions or suspensions. The compositions may be sterilized and/or contain adjuvants, such as preserving, stabilizing, wetting or emulsifying agents, solution promoters, salts for regulating the osmotic pressure and/or buffers. In addition, they may also contain other therapeutically valuable substances. Suitable formulations for transdermal applications include an effective amount of a compound of the present invention with a carrier. A carrier can include absorbable pharmacologically acceptable solvents to assist passage through the skin of the host. For example, transdermal devices are in the form of a bandage comprising a backing member, a reservoir containing the compound optionally with carriers, optionally a rate controlling barrier to deliver the compound to the skin of the host at a controlled and predetermined rate over a prolonged period of time, and means to secure the device to the skin.

The term "sample" refers to a sample of a body fluid, to a sample of separated cells or to a sample from a tissue or an organ. Samples of body fluids can be obtained by well-known techniques and include, preferably, samples of blood, plasma, serum, or urine, more preferably, samples of blood, plasma or serum. Tissue or organ samples may be obtained from any tissue or organ by, e.g., biopsy. Separated cells may be obtained from the body fluids or the tissues or organs by separating techniques such as centrifugation or cell sorting. Preferably, cell-, tissue- or organ samples are obtained from those cells, tissues or organs which express or produce the peptides referred to herein.

The recitation of a listing of elements in any definition of a variable herein includes definitions of that variable as any single element or combination (or sub combination) of listed elements. The recitation of an embodiment herein includes that embodiment as any single embodiment or in combination with any other embodiments or portions thereof.

The invention is directed to an aptamer specifically binding to a skeletal Troponin I protein. The sequence listings disclosed in the content of the disclosure are compiled in the "SEQUENCE LISTING" section. The aptamers includes the following nucleotide sequence:

(SEQ ID NO: 1)
5'-GGG ATG GGG TGG GTG GCC AGC GAT T-3' and (SEQ ID NO: 2)
5'-TTA GGG GTG GTG TGG TTG GCA ATT C-3'.

In other words, the aptamers are single strand of deoxyribonucleic acid (DNA) fragments binding specifically with the skeletal Troponin I protein. In one embodiment, a total length of the aptamer includes 10 to 80 nucleotides. The aptamer of the invention is capable of specifically binding to the skeletal Troponin I protein and a dissociation constant (Kd) between the aptamer and the skeletal Troponin I protein ranges from 5 nanomole (nM) to 37.7 nM, for example, any number in the range inclusive. In one embodiment, the dissociation constant (Kd) between the aptamer and the skeletal Troponin I protein is, for example, 5 nM. In other words, the aptamer and the skeletal Troponin I protein have high affinity and high specificity therebetween. The aptamer of the invention is thus suitable for detecting the skeletal Troponin I protein. The $K_d$ can be calculated by any means known in the art. In one embodiment, the $K_d$ is calculated from the receptor-ligand binding curve which was established by plotting the mean fluorescent intensity (MFI) against different concentrations of the aptamer. The $K_d$ is calculated based on the following equation, with the assumption of one-site saturation:

$$MPI = (B_{max} \times [\text{aptamer}])/(K_d + [\text{aptamer}])$$

where MFI, mean fluorescent intensity; Bmax, maximum MFI reading; [aptamer], concentration of the biotinylated aptamer; $K_d$ dissociation constant.

In particular, since the aptamer of the invention is fabricated through chemical synthesis, for example, the aptamer has the following advantages comparing to antibodies: does not require fabrication in cells or animals, and the fabrication is thus simple, cheap, and has minimal batch difference; the targets can be toxins or molecules lacking immune source, and are not affected by the toxicity tolerance and immune ability of the organism itself; and not easily influenced by environmental factors such as external temperature, humidity, and the like, and can be stored long-term (e.g., days, weeks, months). In addition, in one embodiment, a 5' end of the aptamer can be modified by a thiol group, a biotin, a fluorescent label, a luminescent label, an enzyme, or other substances, so that the 5' end can bind with specific substrates or have labeling characteristics such as light emission. Other aspects include wherein the aptamer is modified with a luminescent label including Firefly luciferase and Renilla luciferase; a fluorescent label including fluorescein isothiocyanate (FITC), phycoerythrin (PE), Cy3, and Cy5; or enzymes including alkaline phosphatase (AP), horse radish peroxidase (HRP).

It should be noted that other than adopting the aptamer of the invention for detecting the skeletal Troponin I protein, the high affinity and high specificity between the aptamer and the skeletal Troponin I protein can also be applied in other biotechnologies. For example, the aptamer can be adopted as a target drug for carrying drugs or directly approaching a site with high expression of the skeletal Troponin I protein to bind with the skeletal Troponin I protein, so as to release drugs or inhibit the function of the skeletal Troponin I protein directly, thereby treating or preventing diseases related to the function of the skeletal Troponin I protein. In order to carry drug, the aptamer can be covalently linked to a drug molecule through the use of suitable linkers and standard chemical processes. As the aptamer of the invention has high affinity to skeletal Troponin I, the drug can be directed to the site with high skeletal Troponin I expression and can be released to inhibit the function of cells, signaling pathway and proteins associated with the skeletal Tropinin I related disorder. In addition, the aptamer may also bind to the skeletal Troponin I protein directly to inhibit the function of skeletal Troponin I protein and its downstream target/pathways, thereby treating or preventing diseases related to the function of the skeletal Troponin I protein. Obviously, other than applying the aptamer for detection or as the target drug, persons of common knowledge in the art should understand that the aptamer of the invention is also suitable for other biotechnologies relying on the high affinity and high specificity of the skeletal Troponin I protein, and the details are thus not illustrated herein.

The invention is further directed to a detection method for a skeletal Troponin I protein. The detection method is suitable for detecting the skeletal Troponin I protein in a sample, and includes the following. An aptamer of the invention is provided. The sample and the aptamer are mixed, such that the skeletal Troponin I protein and the aptamer bind to form a skeletal Troponin I protein-aptamer. The skeletal Troponin I protein or the aptamer in the skeletal Troponin protein-aptamer is then detected. In an embodiment, the detection method for the skeletal Troponin I protein is a fluorescence-based method, and so on. Moreover, this detection method for the skeletal Troponin I protein can increase the stability and convenience, compared to the conventional detection methods. In other words, in one embodiment, since the aptamer can be used to replace the skeletal Troponin I antibody, the detection method for the skeletal Troponin I protein in the invention can be any detection method adopting the binding principles of the skeletal Troponin I antibody and antigen. For example, the skeletal Troponin I protein is coupled on the microspheres via 1-ethyl-3-(3-dimethylaminopropyl)carbodiimide (EDC). The aptamer is then incubated with skeletal Troponin I coated beads in phosphate buffered saline (PBS). The aptamer-bead complex will be formed after one hour incubation at room temperature. In order to detect the presence of the complex, the aptamer bead complex is incubated with the strepavidin-phycoerythrin conjugates and the fluorescence signal, which is expressed in term of mean fluorescent intensity (MFI), is detected using the Luminex 200 3.1 xPONENT System.

The invention is directed to another detection method for the skeletal Troponin I protein. The detection method is suitable for detecting the skeletal Troponin I protein in a sample, and includes the following. A plurality of beads is provided, and the beads are covalently bonded with the skeletal Troponin I protein. The beads and the sample are mixed, such that the skeletal Troponin I protein on the beads bind with the biotinylated aptamer. Strepavidin-phycoerythrin conjugates are then added to the sample mixed with the beads, such that the strepavidin-phycoerythrin conjugates bind with the biotinylated aptamer. The unbound strepavidin-phycoerythrin conjugates are removed. The strepavidin-phycoerythrin conjugates bound to the beads through the biotinylated aptamer are detected.

In an embodiment, the detection method for the skeletal Troponin I protein is, for example, a fluorescence-based method, which includes the following, for example. Skeletal Troponin I proteins in a sample are coated on the magnetic beads, and excessive proteins are washed off. In this step, the skeletal Troponin I proteins are conjugated on the magnetic beads by, for instance, modifying the amine group. A biotinylated aptamer is then added. Here, if the sample includes the skeletal Troponin I protein, the skeletal Troponin I protein then binds the aptamer. Next, the excessive aptamer is washed off, and strepavidin-phycoerythrin conjugates are added. Herein, the strepavidin-phycoerythrin conjugates can form non-covalent bonds with the biotinylated aptamer. Later, the unbound strepavidin-phycoerythrin conjugates are washed off, and the fluorescence signal is detected using the Luminex 200 3.1 xPONENT System. In the present embodiment, as the aptamers and the skeletal Troponin I protein have high affinity (which is in the nanomolar range) and high specificity, the aptamers are capable of recognizing the skeletal Troponin I protein in the sample. In addition, being DNA fragments, the aptamers are not easily influenced by environmental factors such as external temperature, humidity, and the like. That is, the embodiments herein are more stable to extreme conditions (e.g., temperature, humidity) which make them more suitable to use in extreme environments, more stable for longer periods of transport and storage, and thus provide more consistent use and performance than existing methods. In addition, the stability of aptamer is greater than that of antibody, due to the nature of DNA oligo. The great stability of aptamer ensures the simple handling, and high quality of the detections. The detection method for the skeletal Troponin I protein in the present embodiment therefore has high sensitivity, high stability, and high accuracy compared to existing methods known in the art.

There are several advantages of the use of aptamer than that of antibody in skeletal Troponin I detection or therapeutic purpose. For instance, due to the nature of DNA oligo, the stability of aptamer is greater than that of the antibody. The great stability of aptamer ensures the simple handling and high quality of the detections. In addition, when the skeletal Troponin I aptamer acts as a drug carrier or skeletal Troponin I inhibitor, it is less likely to provoke immune responses, compared to the antibody, thus minimizing the risk of therapeutic treatment.

It should be noted that although in the embodiments aforementioned, the skeletal Troponin I protein of the invention are applied in the fluorescence-based method as an example, the detection method for the skeletal Troponin I protein in the invention is not limited thereto. In other words, as the aptamers of the invention have high affinity and high specificity to the skeletal Troponin I protein, the aptamers can be applied in any detection method for detecting the skeletal Troponin I protein. Especially, as the aptamers of the invention can replace the skeletal Troponin I antibodies, the detection method for the skeletal Troponin I protein in the invention can be adopted in any detection method using binding principles of the skeletal Troponin I antibodies and the antigens. These methods are well known to those skilled in the art.

The aptamer of the invention is applied in the Luminex-based method as examples, the detection method for the skeletal Troponin I protein in is not limited thereto. Especially, as the aptamers of the invention can replace the skeletal Troponin I antibodies, for instance, in other fluorescent assays, including Enzyme-linked immunosorbent assay (ELISA), fluorescence microscopic analysis and flow cytometry; calorimetric assay, such as ELISA, immunochemistry staining and lateral flow assay; and chemiluminescent assay, including Western blot and ELISA.

In the following, several experiments are provided to illustrate a method for screening the aptamers of the invention, verify the high affinity and specificity of the aptamers toward the skeletal Troponin I protein, and to depict practical applications of the detection method for the skeletal Troponin I protein in the invention. The following illustrations are provided to describe the invention in detail for the implementation of persons skilled in the art, and not used to limit the scope of the invention.

EXAMPLES

Example 1

Preparation of Oligonucleotide Library and Skeletal Troponin I-Conjugated Beads for Aptamer Selection 1. Establishment of Oligonucleotide Library An oligonucleotide library includes 425 types of oligonucleotides. These oligonucleotides are synthesized by Sangon Biotech (ShangHai) Co. Ltd., China, and each has a 72-mer nucleotide sequence shown in a SEQ ID NO:3. The 72-mer nucleotide sequence includes a random sequence constituted by 25 nucleotides (represented by n), a 5'-primer region constituted by 23 nucleotides, and a 3'-primer region constituted by 24 nucleotides:

```
                                           (SEQ ID NO: 3)
5'-GGG ACC ATG GAA TAA ACG CTG AA-[n]25-ATC AGC
AGG AAG CTC GAG ACA GGC-3'.
```

Here, n represents a nucleotide selected from adenine (a), thymine (t), cytosine (c), and guanine (g). The 5'-primer region and the 3'-primer region are respectively designed to be nucleotide sequences recognized by GoTaq DNA polymerase (Promega, USA) for performing a polymerase chain reaction (PCR). Then, a suitable amount of oligonucleotide library is dissolved in phosphate buffered saline (PBS) to obtain a 25 micro-molar (uM) oligonucleotide library stock solution for use 2. Fabrication of Skeletal Troponin I Protein-Conjugated Beads One hundred micro-liter (uL) Dynabeads M-270 Carboxylic Acid (Cat. No. 143.06D, Invitrogen, USA, concentration of 2×109 bead/milli-liter (mL)) are extracted to an eppendorf using a pipette, and the eppendorf is placed in a magnet (MagnaRack, Invitrogen, USA), so that the Dynabeads M-270 Carboxylic Acid are attracted by the magnet so as to move toward the magnet and adhere to an inside wall of the eppendorf. Residues in the eppendorf not attracted by the magnetic field are removed. The Dynabeads M-270 Carboxylic Acid are rinsed with 100 uL of 0.01 molar (M) sodium hydroxide and, subsequently, 100 uL of deionized water. Two hundred micro-liter of 1-ethyl-3-(3-dimethylaminopropyl) carbodiimide (EDC) (76 mg/ml) is added to the eppendorf and mixed for 10 minutes. The excess EDC is removed and 60 micro-gram (ug) of skeletal Troponin I protein [in 2-(N-morpholino)ethanesulfonic acid buffer] are added to the eppendorf and mixed well. The eppendorf is then moved out from the magnet and placed at room temperature for 30 minutes, so that the skeletal Troponin I proteins are conjugated to the Dynabeads M-270 Carboxylic Acid to form skeletal Troponin I protein-conjugated beads (referred as beads A). Thereafter, the eppendorf is placed inside the magnet, such that the beads A are adsorbed to the inside wall of the eppendorf. Residues in the eppendorf that are not attracted by the magnetic field are removed and the beads A are washed three times with phosphate buffered saline (PBS). Subsequently, the beads A are resuspended in 100 uL PBS and placed under 4° C. for storage.

Example 2

Screening of Aptamers Having Affinity to Skeletal Troponin I Protein

The oligonucleotide library (from Experiment Example 1) or the PCR product is used to perform a following competitive test. A hundred micro-liter of the oligonucleotide library or the PCR product is mixed well with 12 uL of Dynabeads M-270 Carboxylic Acid. Subsequently, the reactant is incubated at room temperature with agitation for 1 hour. Next, the residue is collected using a magnet and is added to 2 uL to 12 uL of beads A, incubated at room temperature with agitation for 1 hour. Later, the beads A are washed three times with PBS. A PCR reaction is then performed to the beads A with the pair of primers stated in the following (including the forward primer F1 and the reverse primer R1) and referring to the reaction conditions listed in Table US-00002.

TABLE-US-00001

```
Forward primer F1                    (SEQ ID NO: 4)
5'-GGG ACC ATG GAA TAA ACG CTG AA-3'

Reverse primer R1                    (SEQ ID NO: 5)
5'-GCC TGT CTC GAG CTT CCT GCT GAT-3'
```

TABLE-US-00002 Reaction Conditions of PCR Contents of PCR Reagent Volume (uL)
Forward primer F1 (10 uM) 3 uL
Reverse primer R1 (10 uM) 3 uL
dNTPs (10 mM) 5 uL
GoTaq DNA polymerase (5U/uL) 0.5 uL
5× Reaction buffer 20 uL
$MgCl_2$ (25 mM) 15 uL
Deionized water is added to a total volume of 100 uL.
Operation conditions: perform denaturing for 2 min at 95° C.; perform 13 to 22 cycles of: denaturing for 30 second (sec) at 95° C., primer annealing for 30 sec at 56° C., and elongation for 30 sec at 72° C.; finally stand for 10 min at 72° C.

In order to assess the quality of the PCR products, the PCR products obtained therefrom are separated by performing an electrophoresis in a 2.5% agarose gel. The agarose gel is then stained with Gel-Red and observed under the GE ImageQuant 350 imaging system.

Upon the completion of the PCR reaction, the PCR products are mixed with the beads A, in order to perform another round of competitive test. The competitive test and the PCR amplification are repeated for 15 times. Finally, the final product is collected to perform the following experiment.

Figure 2:
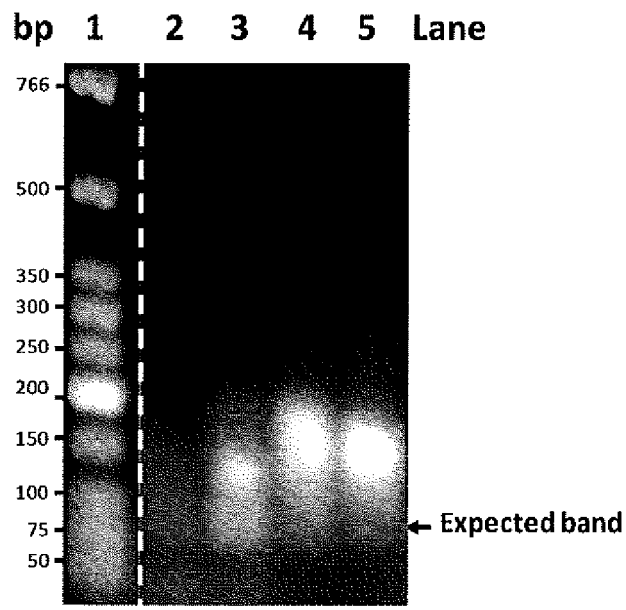
FIG. 2 illustrates results of an agarose gel electrophoresis of polymerase chain reaction (PCR) products obtained from an aptamer pool after a competitive test. The aptamer pool after A) single round, and; B) fifteen rounds of competition test were amplified using PCR method. In order to obtain an optimal amplification cycle, PCR amplicons were collected at different PCR cycles and were submitted to gel electrophoresis analysis. The PCR amplicons were separated using 2.5% agarose gel and visualized using Gel-Red under the GE ImageQuant 350 imaging system (GE Healthcare, USA). Lane 1: DNA ladder; lane 2-5: 13th, 16th, 19th and 22nd PCR cycle, respectively.
Figure 2:
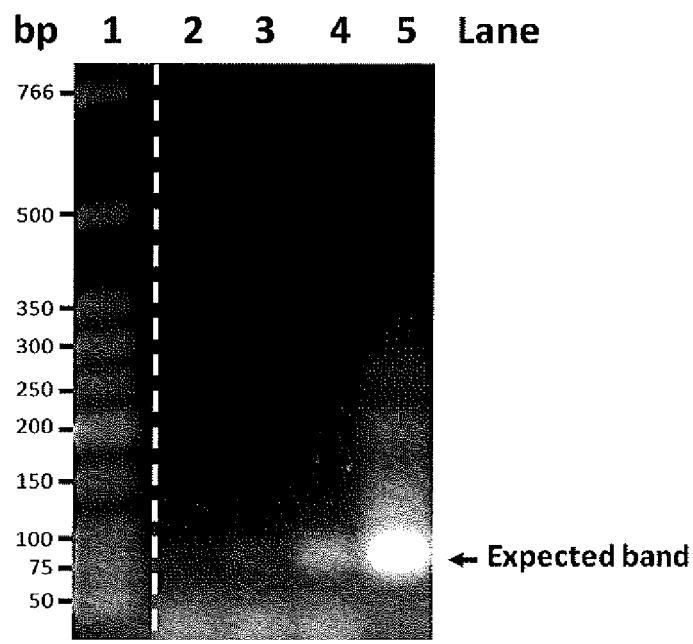

Results: FIG. 2 illustrates the result of the agarose gel electrophoresis of PCR products obtained from a PCR reaction performed using the primers after A) single round, and; B) fifteen rounds of competitive test. In order to obtain an optimal amplification cycle, PCR amplicons were collected at different PCR cycles and were submitted to gel electrophoresis. The PCR amplicons were separated using 2.5% agarose gel and visualized using Gel-Red under the GE ImageQuant 350 imaging system (GE Healthcare, USA). Lane 1: DNA ladder; lane 2-5: 13th, 16th, 19th and 22nd PCR cycle, respectively. bp: base pair. As shown in FIG. 2, there is a specific band with a size about 72 basepair (bp). This indicates that the beads A isolates the anti-skeletal Troponin I aptamers. In addition, more chimeric products were detected in the 1st round (FIG. 2A) of competitive test, compared to the 15th round (FIG. 2B). After 15 rounds of competitive test, a dominant aptamer may present within the aptamer pool. The overexpression of the dominant aptamer may increase the homology of the aptamer pool, reduce the occurrence of recombination events and, thus, avoid the formation of chimeric products. To conclude, after 15 rounds of competitive test, we isolated an anti-skeletal Troponin I aptamer, which dominates the aptamer pool as proved by the following sequencing experiment (Experiment Example 3).

Example 3

Sequencing of Aptamers Having Affinity to Skeletal Troponin I Protein

The final PCR product (from Experiment Example 2) is used to perform a following labeling reaction for next generation sequencing. A PCR reaction is performed using the final PCR product (from Experiment Example 2) with the pair of primers stated in the following (including the forward primer F2 and the reverse primer R2) and referring to the reaction conditions listed in Table US-00004.
TABLE-US-00003

```
Forward primer F2                         (SEQ ID NO: 6)
5'-CCA TCT CAT CCC TGC GTG TCT CCG ACT
CAG ATG ATA GGG ACC ATG GAA TAA ACG CTG AA-3'

Reverse primer R2                         (SEQ ID NO: 7)
5'-CCT CTC TAT GGG CAG TCG GTG ATG CCT
GTC TCG AGC TTC C-3'
```

TABLE-US-00004 Labeling Reaction Condition of PCR Contents of PCR Reagent Volume (uL)
Forward primer F2 (10 uM) 2.5 uL
Reverse primer R2 (10 uM) 2.5 uL
dNTPs (10 mM) 2.5 uL
GoTaq DNA polymerase (5U/uL) 0.25 uL
5× Reaction buffer 10 uL
$MgCl_2$ (25 mM) 7.5 uL
Deionized water is added to a total volume of SOUL. Operation conditions: perform denaturing for 2 min at 95° C.; perform 13 to 22 cycles of: denaturing for 30 second (sec) at 95° C., primer annealing for 30 sec at 56° C., and elongation for 30 sec at 72° C.; finally stand for 10 min at 72° C.

The labeled PCR products are purified using Minelute Gel Purification kit (Qiagen, USA) according to manufacturer protocol. The purified products are submitted for the next generation sequencing.

Example 4

Evaluation of Affinity of Aptamer to Skeletal Troponin I Protein

In the present experiment, the aptamers screened out from Experiment Example 3 are analyzed with the Luminex 200 3.1 xPONENT System, so as to evaluate the affinity of the aptamers to the skeletal Troponin I protein from a dissociation constant Kd of the skeletal Troponin I-aptamers.

Firstly, the skeletal Troponin I protein is coupled on the MagPlex microspheres. Fifty micro-liter (uL) MagPlex microsphere (Cat. No. MC10064-01, Luminex, USA, concentration of 1.25×107 microspheres/milli-liter (mL)) are extracted to an eppendorf using a pipette, and the eppendorf is placed in a magnet (MagnaRack, Invitrogen, USA), so that the MagPlex microspheres are attracted by the magnet so as to move toward the magnet and adhere to an inside wall of the eppendorf. Residues in the eppendorf not attracted by the magnetic field are removed. The MagPlex microspheres are rinsed with 100 uL of 0.01 molar (M) sodium hydroxide and, subsequently, 100 uL of deionized water. Two hundred micro-liter of 1-ethyl-3-(3-dimethylaminopropyl)carbodiimide (EDC) (76 mg/ml) is added to the eppendorf and mixed for 10 minutes. The excess EDC is removed and 30 microgram (ug) of skeletal Troponin I protein [in 2-(N-morpholino) ethanesulfonic acid buffer] are added to the eppendorf and mixed well. The eppendorf is then moved out from the magnet and placed at room temperature for 60 minutes, so that the skeletal Troponin I proteins are conjugated to the MagPlex microspheres to form skeletal Troponin I protein-conjugated beads (referred as beads B). Thereafter, the eppendorf is placed inside the magnet, such that the beads B are adsorbed to the inside wall of the eppendorf. Residues in the eppendorf that are not attracted by the magnetic field are removed and the beads B are washed three times with phosphate buffered saline (PBS). Subsequently, the beads B are resuspend in 50 uL PBS and placed under 4° C. for storage.

In order to determine the dissociation constant (Kd) between the skeletal Troponin protein and its aptamer, the beads B (5000 microspheres) are incubated with the indicated amount of a biotinylated aptamer (SEQ ID NO: 1 or SEQ ID NO: 2) for 1 hour at room temperature. The beads B are rinsed with 200 uL PBS for three times and are subsequently incubated with the strepavidin-phycoerythrin conjugates (4 ug/mL) for 30 minutes. The beads B are the rinsed with 200 uL PBS for three times and are resuspended in 125 uL PBS. The fluorescence signals are measured using the Luminex 200 3.1 xPONENT System and are expressed in mean fluorescence intensity.

Figure 3:
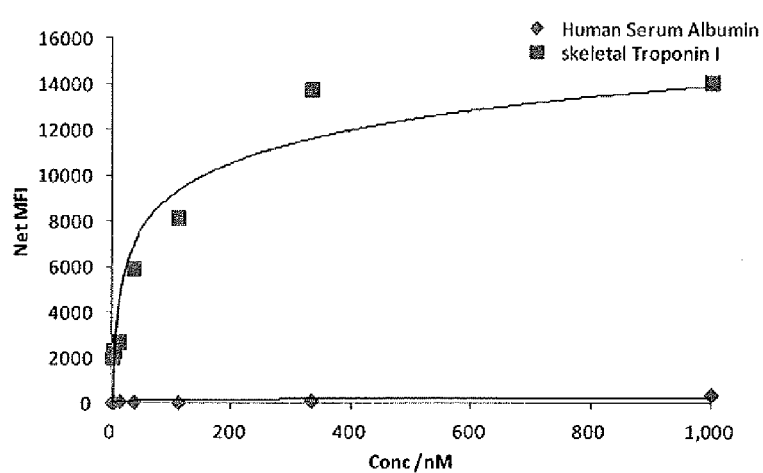
FIG. 3 is a receptor-ligand binding curves measured under the indicated aptamer concentrations, detected using the Luminex 200 3.1 xPONENT System (Millipore, USA). In brief, the MagPlex microspheres were coated with the skeletal Tropinin I protein. The microspheres were then incubated with the indicated amounts of a biotinylated aptamer. Subsequently, strepavidin-phycoerythrin conjugates were added and the amount of strepavidin-phycoerythrin conjugates bound to the beads through the biotinylated aptamer were detected. A) SEQ ID NO; 1, with dissociation constant (Kd) of 37.7 nM, and; B) SEQ ID NO: 2, with Kd of 5 nM. Results shown are mean fluorescent intensity and minimum of 100 events were collected. Human serum albumin was used as negative control.
Figure 3:
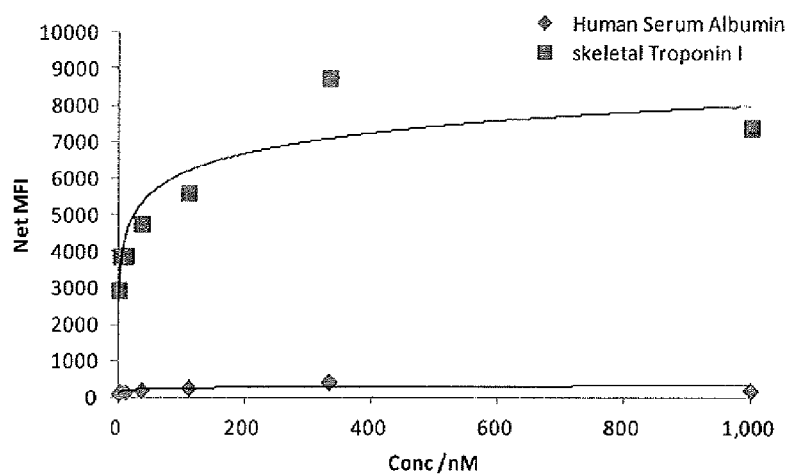

Results: FIG. 3 is the receptor-ligand binding curves measured under the indicated aptamer concentrations, detected using the Luminex 200 3.1 xPONENT System (Millipore, USA). In brief, the MagPlex microspheres were coated with the skeletal Tropinin I protein. The microspheres were then incubated with the indicated amounts of a biotinylated aptamer. Subsequently, strepavidin-phycoerythrin conjugates were added and the amount of strepavidin-phycoerythrin conjugates bound to the beads through the biotinylated aptamer were detected. A) SEQ ID NO: 1, with dissociation constant (Kd) of 37.7 nM, and; B) SEQ ID NO: 2, with Kd of 5 nM. Results shown are mean fluorescent intensity and minimum of 100 events were collected. Human serum albumin was used as negative control. As shown in FIG. 3, the anti-skeletal Troponin I aptamers specifically recognize the skeletal Troponin I protein and differentiate the skeletal Troponin I protein from human serum albumin. The dissociation constant of both aptamer ranges from 5 nM to 37 nM, in which SEQ ID NO:2 has a higher binding affinity towards the skeletal Troponin I protein than that of SEQ ID NO:1.

In summary, the aptamers of the invention specifically bind to the skeletal Troponin protein and have high affinity to the skeletal Troponin I protein. Therefore, the aptamers of the invention can be widely applied in the detection method for the skeletal Troponin I protein and biotechnologies such as skeletal Troponin I protein target drugs. In particular, since the aptamers of the invention have simple fabrication, low cost, minimal batch difference and storage stability, the detection method for the skeletal Troponin I protein adopting the aptamers has high sensitivity, high stability, and high accuracy, and can be used in clinical examination and academic research for assessment and prevention of disease.

It will be apparent to those skilled in the art that various modifications and variations can be made to the structure of the disclosed embodiments without departing from the scope or spirit of the disclosure. In view of the foregoing, it is intended that the disclosure cover modifications and variations of this disclosure provided they fall within the scope of the following claims and their equivalents.

What is claimed is:

1. An aptamer that specifically binds to a skeletal Troponin I protein comprising one of the following nucleotide sequences:

(SEQ ID NO: 1)
5'-GGG ATG GGG TGG GTG GCC AGC GAT T-3', (SEQ ID NO: 2)
5'-TTA GGG GTG GTG TGG TTG GCA ATT C-3'.

2. The aptamer of claim 1, wherein the dissociation constant ($K_d$) between the aptamer and the skeletal Troponin I protein ranges from 5 nanomole (nM) to 37.7 nM.

3. The aptamer of claim 1, having a 5' end modified by a thiol group, a biotin label, a luminescent label; a fluorescent label; or an enzymes.

4. A detection method for detecting the skeletal Troponin I protein in a sample, the detection method comprising: providing the aptamer of claim 1; mixing the sample and the aptamer, such that the skeletal Troponin I protein in the sample and the aptamer bind to form a skeletal Troponin I-aptamer complex; and detecting the skeletal Troponin I protein or the aptamer in the skeletal Troponin I-aptamer complex.

5. The detection method for the skeletal Troponin I protein of claim 4, wherein the aptamer is labeled with a thiol group, a biotin label, a luminescent label; a fluorescent label; or an enzyme.

6. A detection method for a skeletal Troponin I protein, adapted for detecting the skeletal Troponin I protein in a sample, the detection method comprising: providing a plurality of beads covalently bonded to the skeletal Troponin I protein; mixing the beads and an aptamer of claim 1 labeled with a biotin label; a luminescent label; a fluorescent label; or an enzyme; such that the skeletal Troponin I protein on the beads bind with the labeled aptamer; adding strepavidin-phycoerythrin conjugates to the sample mixed with the beads, such that the strepavidin-phycoerythrin conjugates bind with the labeled aptamer; removing the unbound strepavidin-phycoerythrin conjugates; and detecting the strepavidin-phycoerythrin conjugates bound to the beads through the labeled aptamer.

7. The detection method for the skeletal Troponin I protein of claim 6, wherein the labeled aptamer is labeled with a biotin label.

8. An aptamer-bead complex comprising an aptamer of claim 1.

9. The aptamer-bead complex of claim 8 further comprising a label moiety.

10. A method of making a complex of claim 8 comprising mixing beads with an aptamer of claim 1.

11. The method of claim 10, further comprising mixing a strepavidin-phycoerythrin conjugate with the beads and aptamer.

12. A kit comprising the aptamer of claim 1 and instructions for use to detect Troponin I.

13. The kit of claim 12, wherein the aptamer is conjugated to a bead.

14. The method of claim 4, further comprising communicating to a health care provider the level of Troponin I detected.

15. A composition comprising skeletal Troponin I protein on a head, an aptamer of claim 1, and a strepavidin-phycoerythrin conjugate.

16. The composition of claim 15, wherein the aptamer is biotinylated.

\* \* \* \* \*

SEQUENCE LISTING

<160> NUMBER OF SEQ ID NOS: 7

<210> SEQ ID NO 1
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1
gggatggggt gggtggccag cgatt                                        25

<210> SEQ ID NO 2
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2 ttagggtgg tgtggttggc aattc                                         25

<210> SEQ ID NO 3
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (24)..(48)
<223> OTHER INFORMATION: a, c, t or g

<400> SEQUENCE: 3
gggaccatgg aataaacgct gaannnnnnn nnnnnnnnnn nnnnnnnnat cagcaggaag   60
ctcgagacag gc                                                       72

<210> SEQ ID NO 4
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
gggaccatgg aataaacgct gaa                                          23

<210> SEQ ID NO 5
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
gcctgtctcg agcttcctgc tgat                                         24

<210> SEQ ID NO 6
<211> LENGTH: 59
<212> TYPE: DNA
<213> ORGANISM: Artificial Sequence

```
<220> FEATURE:
<223> OTHER INFORMATION: Description of Artificial Sequence: Synthetic
      primer

<400> SEQUENCE: 6
ccatctcatc cctgcgtgtc tccgactcag atgataggga ccatggaata aacgctgaa      59

<210> SEQ ID NO 7
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
cctctctatg ggcagtcggt gatgcctgtc tcgagcttcc                           40
```